(12) United States Patent
Nagase et al.

(10) Patent No.: US 7,056,446 B2
(45) Date of Patent: Jun. 6, 2006

(54) METHOD OF MANUFACTURING NANO-GAP ELECTRODE

(75) Inventors: Takashi Nagase, Tokyo (JP); Tohru Kubota, Tokyo (JP); Shinro Mashiko, Tokyo (JP)

(73) Assignee: Communications Research Laboratory, Independent Administrative Institution, Tokyo (JP)

( * ) Notice: Subject to any disclaimer, the term of this patent is extended or adjusted under 35 U.S.C. 154(b) by 118 days.

(21) Appl. No.: 10/662,886

(22) Filed: Sep. 16, 2003

(65) Prior Publication Data

US 2004/0161708 A1    Aug. 19, 2004

(30) Foreign Application Priority Data

Feb. 14, 2003    (JP) .............................. 2003-036568

(51) Int. Cl.
   *B44C 1/22*    (2006.01)
(52) U.S. Cl. .............................. 216/57; 216/41; 216/51; 216/66; 216/94; 430/296; 430/313; 204/192.1; 250/492.3; 977/722
(58) Field of Classification Search ................ 216/41, 216/51, 66, 94, 57; 250/492.3; 204/192.1; 430/5, 313, 296; 977/722
   See application file for complete search history.

(56) References Cited

U.S. PATENT DOCUMENTS

| 4,085,330 | A | * | 4/1978 | Wolfe ....................... 250/492.2 |
| 4,293,374 | A | * | 10/1981 | Chaudhari et al. ............. 216/12 |
| 5,569,569 | A | * | 10/1996 | Goto et al. ..................... 430/5 |
| 5,773,843 | A | * | 6/1998 | Nakamura et al. ............. 257/30 |
| 6,245,249 | B1 | * | 6/2001 | Yamada et al. ............... 216/33 |
| 2003/0067259 | A1 | * | 4/2003 | Nishimura ................... 313/310 |

OTHER PUBLICATIONS

R.L. Kubena, et al, A Low Magnification Focused Ion Beam System with 8 nm spot size, J. Vac. Sci. Technol. B9, 3079-3083 (1991).
S. Matsui, et al, High Resolution Focused Ion Beam Lithography, J. Vac. Sci. Technol. B9, 2622-2632 (1991).
M.A. Reed, Molecular-Scale Electronics, Proc. IEEE, 87, 652-658 (1999).
A. Aviram, et al, Molecular Electronics II, New York Academy of Sciences, New York (2002)—Table of Contents.
Y. Wada, et al., Prospects and Problems of Single Molecule Information Devices, Jpn. J. Appl. Phys. Part 1, 39, 3835-3849 (2000).

(Continued)

*Primary Examiner*—Shamim Ahmed
(74) *Attorney, Agent, or Firm*—Foley & Lardner LLP

(57) ABSTRACT

A method of easily manufacturing a nano-gap electrode by using a focused ion beam lithography includes a layer depositing step of depositing an electrode layer and a metal mask layer in this order on an insulating substrate, a mask pattern forming step of etching the metal mask layer by using the focused ion beam and thereby forming a mask pattern, a dry etching step of transferring a pattern to the electrode layer by dry etching, and a wet etching step of removing the metal mask layer by using a solution that selectively dissolves the metal mask layer compared to the electrode layer.

19 Claims, 5 Drawing Sheets

OTHER PUBLICATIONS

Technical Report IEICE, vol. 102, No. 303, 2002, pp. 33-36.
Nice, vol. 2, No. 3, 2002, pp. 3-7.
Conference Program of ICNME, Dec. 10-12, 2002, pp. 221-222.

* cited by examiner

METHOD OF MANUFACTURING NANO-GAP ELECTRODE

CROSS-REFERENCE TO RELATED PATENT APPLICATIONS

Japanese Priority Application JP 2003-36568, filed Feb. 14, 2003 including the specification, drawings, claims and abstract, is incorporated herein by reference in its entirety.

BACKGROUND OF THE INVENTION

The invention relates to a method of manufacturing a nano-gap electrodes by focused ion beam lithography, and in particular, to a method of manufacturing nano-gap electrodes by a focused ion beam lithography using a metal thin film as a mask.

In recent years, research has been actively conducted on molecular electronic devices using single organic molecules. This is because semiconductor process technology is approaching its miniaturization limits and because there is produced a concept of applying a single organic molecule, which is essentially as small in size as a few nanometers, to a device (see for example, "Molecular Electronics II", New York Academy of Sciences, New York (2002)). In order to realize molecular electronic devices, there are problems to be solved such as molecular alignment technology. As the first step, it is necessary to measure the electrical properties of single organic molecules. The measurement enables one to correctly understand the influence of the characteristics of organic molecules such as molecular orbits and functionality on the electric conduction characteristics of single organic molecules. For this end, pairs of metal electrodes which have a gap of several nanometers and can sandwich the single organic molecule (nano-gap electrode) are required.

Generally, in order to manufacture nano-gap electrodes, electron beam lithography has been used. However, the producible minimum gap length manufactured using this method is restricted to about 20 nm because of electron scattering (proximity effect). Focused ion beam (FIB) lithography has also been used to manufacture nanostructures, The proximity effect of FIB lithography can be neglected because ions, which are larger in mass than electrons, are used. Moreover, the minimum diameter of the FIB is relatively small (as small as 10 nm). An example is disclosed in which positive resist line patterns having widths from 8 nm to 10 nm is manufactured using FIB lithography (see for example, R. L. Kubena, J. W. Ward, F. P. Stratton, R. J. Joyce and G. M. Atkinson, "A Low Magnification Focused Ion Beam System with 8 nm Spot Size", J. Vac. Sci. Technol. B9, 3079–3083 (1991)). As described above, in general, the FIB lithography can make smaller electrode gaps than the electron beam lithography.

Generally, in the FIB lithography, an organic resist is exposed by ion beam and then is developed (i.e., patterned) and then a mask pattern is transferred to an electrode. In the FIB lithography, in order to reduce the resist's exposure region by scattered ions, an ion beam at a high acceleration voltage of about several hundreds kV is used (for example, see R. L. Kubena, J. W. Ward, F. P. Stratton, R. J. Joyce and G. M. Atkinson, "A Low Magnification Focused Ion Beam System with 8 nm Spot Size", J. Vac. Sci. Technol. B9, 3079–3083 (1991); S. Matsui, Y. Kojima, Y. Ochiai and T. Honda, "High-Resolution Focused Ion Beam Lithography", J. Vac. Sci. Technol. B9, 2622–2632 (1991)). The highly accelerated ions can penetrate a metal at a depth of about 100 nm from the surface. Thus, when a nano-gap electrode is made using the FIB lithography, the ions can easily pass through a metal electrode and may reach an underlying insulating substrate. This presents a problem in that the insulating characteristic of the nano-gap electrode may be changed by the FIB.

FIG. 1 shows a numerical simulation result of a $Ga^+$ ion penetration depth into a Au substrate. A TRIM (the Transport of Ion in Matter), IBM (1998)) which is a typical program for the numerical simulation of ion implantation using Monte Carlo Method was used. It is evident from FIG. 1 that the ion penetration depths at high acceleration voltages of 100 kV and 260 kV reaches about 70 nm and 150 nm at the maximum depth, respectively.

The ion implantation into the insulating substrate can be reduced by using the metal electrode thicker than the ion penetration length. On the other hand, in order to fabricate narrow gaps, it is necessary to use a thin organic resist film (that is, required to reduce ion scattering in the resist as much as possible). Using the thin resist film presents a problem that the resist is not durable when a thick electrode is transferred by dry etching. Moreover, in the FIB lithography, it is necessary to expose the resist at the low amount of ions. However, this presents a problem in that it is generally difficult to control the low level of ion exposure. For these reasons, the nano-gap electrode can not always be easily manufactured by the conventional FIB lithography using the organic resist.

SUMMARY OF THE INVENTION

A first preferred embodiment of the present invention provides a method of manufacturing a nano-gap electrode that includes a layer depositing step of depositing an electrode layer and a metal mask layer in this order on an insulating substrate; a mask pattern forming step of etching the metal mask layer by using a focused ion beam and thereby forming a mask pattern; a dry etching step of transferring the pattern to the electrode layer by dry etching; and a wet etching step of dissolving and removing the metal mask layer by using a solution that dissolves the metal mask layer more easily than the electrode layer. According to this method of manufacturing a nano-gap electrode, the metal layer is used like a conventional resist, so that it is possible to make the electrode having a microscopic gap between two electrode portions without impairing the insulating ability of the insulating substrate.

The first embodiment preferably includes a step of forming an adhesion layer between the insulating substrate and the electrode layer for enhancing adhesion of the insulating substrate and the electrode layer. This adhesion layer may act as the electrode layer. Since the adhesion layer can enhance the adhesion of the insulating substrate and the electrode layer, it is possible to prevent the electrode layer from being separated from the insulating substrate.

In the first embodiment, preferably, the thickness of the electrode layer is larger than a maximum ion penetration length, which is a length when the focused ion beam is most deeply penetrated into electrode in the mask pattern forming step. This extent of thickness of the electrode layer can prevent the characteristics of the insulating substrate in the gap from being changed by ion implantation.

In the first embodiment, preferably, the thickness of the metal mask layer ranges from 10 nm to 400 nm. This extent of thickness of the metal mask layer can resist etching when the electrode layer is etched.

In the first embodiment, preferably, ions impact against metal mask layer at a dose from $10^{15}$ to $10^{21}$ ions/cm² in the mask pattern forming step. In conventional FIB lithography using an ordinary organic resist, it is essential only to applying ions at a dose from $10^{12}$ to $10^{14}$ ions/cm$^2$. However, in order to etch the metal layer, it is preferable to make more ions impact against the metal layer.

In the first embodiment, preferably, not only the metal mask layer but also the electrode layer is removed by 1 nm to 40 nm on an average in the mask pattern forming step. Some undulations are formed at the boundary surface between the metal mask layer and the electrode layer and the metal mask layer including these undulations can effectively be removed.

In the first embodiment, preferably, a gap between electrode portions ranges from 2 nm to 12 nm. If the gap between electrode portions ranges from 2 nm to 12 nm, it is possible to measure the electric conduction characteristics of a single organic molecule.

In the first embodiment, preferably, titanium is used for the metal mask layer. A metal having electric conductivity and solvent resistance such as gold and platinum is used for the electrode layer. A metal that is more susceptible to acid and harder than electrode metals is suitable for the metal mask layer of the invention. Titanium satisfies this requirements and hence is suitable for the metal mask layer.

In the first embodiment, preferably, gold is used for the electrode layer. Gold has excellent electric conduction and chemical resistance and is comparatively soft and hence is suitable for the electrode layer.

In the first embodiment, preferably, a gallium ion beam accelerated by an applied voltage from 10 kV to 200 kV is used as the focused ion beam. By using the high-speed ion beam like this, it is possible to perform more suitable etching.

In the first embodiment, preferably, a focused ion beam having a minimum diameter from 5 nm to 100 nm is used as the focused ion beam. By using the ion beam having a minimum diameter as described above, it is possible to effectively produce a narrow nano gap. The minimum diameter is defined as the full width of half maximum (FWHM) at the intensity distribution of the focused ion beam.

In accordance with a second preferred embodiment, a method of manufacturing a nano-gap electrode whose two electrode portions have a gap ranging from 4 nm to 6 nm that includes a deposition step of vacuum vapor-depositing a Pt layer from 10 nm to 15 nm in thickness as an adhesion layer and an Au layer from 60 nm to 80 nm in thickness as an electrode layer, and a Ti layer from 40 nm to 50 nm in thickness as a metal mask layer in this order on an insulating substrate (layer) from 200 nm to 400 nm in thickness, by a sputter vapor-depositing method; a mask pattern forming step of making Ga$^+$ ions impact against the metal mask layer at a dose from $10^{17}$ to $10^{18}$ ions/cm$^2$ by using a focused ion beam including the Ga$^+$ ions and having a minimum diameter from 10 nm to 15 nm and accelerated by an acceleration voltage from 25 kV to 40 kV and thereby etching the metal mask layer and forming a mask pattern; a dry etching step of etching an electrode layer including the Au layer and the Pt layer by sputter etching using Ar$^+$ ions and thereby patterning the electrode layer; and a wet etching step of dipping the metal mask layer in an acid water solution containing sulfuric acid and thereby removing the metal mask layer. According to the second embodiment, it is possible to manufacture the nano-gap electrode with reliability.

In the second embodiment, preferably, the thickness of the insulating substrate (layer) is 300 nm; the thickness of the Pt layer is 12 nm; the thickness of the Au layer is 70 nm; the thickness of the Ti layer is 45 nm; the acceleration voltage of the Ga$^+$ ions is 30 kV; the minimum diameter of the Ga$^+$ ion beam is 12 nm, and the gap between two electrode portions of the nano-gap electrode is 5 nm. According to this preferred embodiment, it is possible to manufacture the nano-gap electrode with reliability.

A third preferred embodiment provides a nano-gap electrode in which a gap between two electrode portions constituting an electrode layer ranges from 4 nm to 6 nm. By using the nano-gap electrode having such a narrow gap, it is possible to measure the electric conduction characteristics of a single organic molecule.

The third embodiment preferably includes an insulating substrate and the electrode layer formed on the insulating substrate and the electrode layer preferably contains either or both of gold and platinum.

BRIEF DESCRIPTION OF THE DRAWINGS

FIG. 2A is a schematic diagram of a mask pattern forming step. FIG. 2B is a schematic diagram of a dry etching step. FIG. 2C is a schematic view after a wet etching step.

DETAILED DESCRIPTION OF THE PREFERRED EMBODIMENTS

Figure 2:
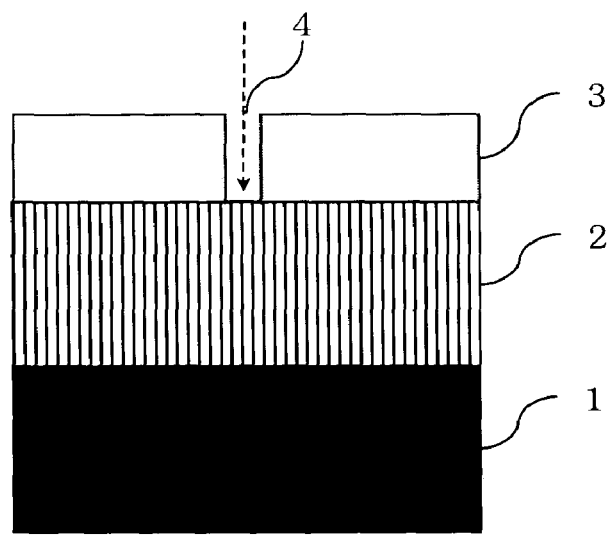
FIG. 2 is a schematic diagram of a process for manufacturing a nano-gap electrode in accordance with a first embodiment of the invention.
Figure 2:
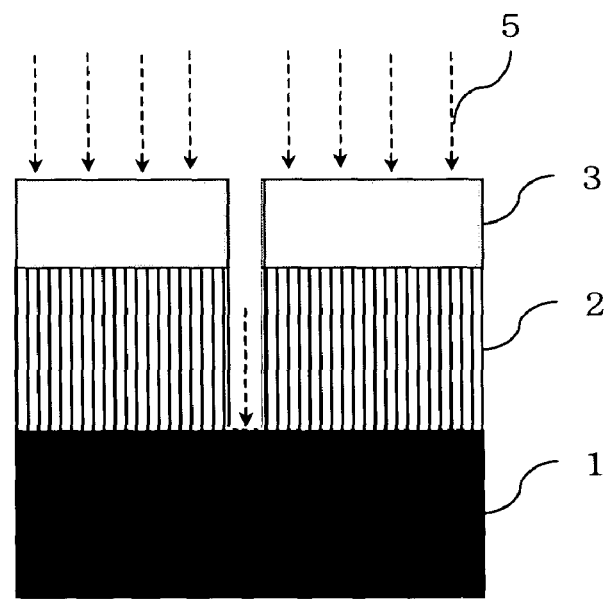
Figure 2:
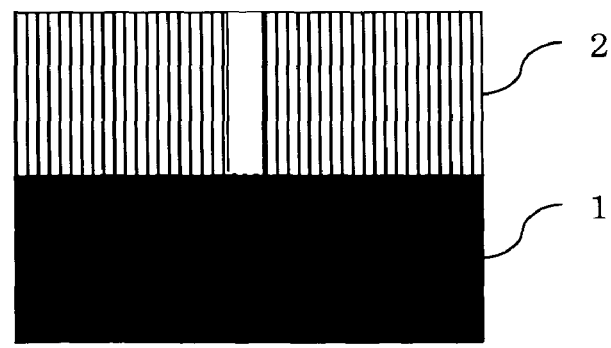

FIG. 2 shows a process of manufacturing a nano-gap electrode in accordance with a first embodiment of the invention (hereinafter referred to as a first embodiment). In this first embodiment, an electrode layer 2 and a metal mask layer 3 are evaporated in this order onto an insulating substrate 1. The metal mask layer 3 is used as a dry etching mask of the electrode layer 2 underlying it. The process of manufacturing the nano-gap electrode includes the following steps. First, the electrode layer 2 and the metal mask layer 3 are deposited in this order on the insulating substrate 1 (layer depositing step). Then, as shown in FIG. 2A, the metal mask layer 3 is etched by using a focused ion beam 4 to form a mask pattern (mask pattern forming step). Then, as shown in FIG. 2B, the electrode layer 2 is masked by a mask pattern formed in the mask pattern forming step and the pattern is transferred to the electrode layer 2 by a dry etching process. In the dry etching process, an etching gas 5 impacts against the metal mask layer 3 and the exposed portion(s) of the electrode layer 2 which is not masked. Then, as shown in FIG. 2C, the metal mask layer 3 is selectively dissolved and removed by using a solution that more easily dissolves the metal mask layer 3 than the electrode layer 2 (wet etching process). In this manner, the nano-gap electrode is manufactured.

It should be noted that any other suitable selective etching processes may be used instead. Thus, the exposed portions of the electrode layer 2 may be etched by any suitable dry or wet etching medium which selectively etches the material of the electrode layer compared to the material of the mask layer 3. Likewise, the metal mask layer 3 may be removed from the patterned electrode layer 2 by any suitable dry or wet etching medium which selectively etches the material of the mask layer 3 compared to the material of the electrode layer 2. Thus, preferably, an organic resist is not used in the patterning of the nano-gap electrode.

In the present specification, the term "nano-gap electrode" means a pair of electrodes having a gap of several nanometers that can sandwich a single organic molecule, that is, an electrode whose two electrode portions have a gap of several nanometers. The gap between the electrode portions preferably ranges from $5/12$ to $1/2$ of the minimum diameter of a FIB, and preferably, from 2 nm to 12 nm, and more preferably, from 2 nm to 10 nm, and still more preferably, from 3 nm to 6 nm. Here, in the present specification, the gap between the nano-gap electrode portions means an average gap. In the example of the invention, which will be later described, a nano-gap electrode having a gap between the electrode portions of 5 nm could be produced by using a FIB having a minimum diameter of 12 nm. That is, it is possible to produce a nano-gap electrode in which a gap between its electrode portions is not larger than one half of the minimum diameter of the FIB. For example, at present, an apparatus capable of controlling the minimum diameter of the FIB to about 4 nm or 5 nm is developed, so using such an apparatus makes it possible to produce a nano-gap electrode in which a gap between its electrode portions is 2 nm or 2.5 nm.

Any suitable materials may be used for the substrate 1, electrode layer 2 and metal mask layer 3. Preferably, the substrate 1 is an electrically insulating substrate. An insulating substrate is not limited to a particular material or materials as long as it has an insulating property. For example, an insulating substrate 1 can be made of glass, quartz, silicon oxide, coating type silicon oxide film (spin on glass ("SOG")), sapphire, metal oxide such as aluminum oxide and titanium oxide, calcium fluoride, and plastics such as polyethylene, polypropylene, polystyrene, AS, ASB, polyacetal, polyimide, polyalkylene terephthalate, polysulfone, polyacrylate, fluororesin, silicone, phenolic resin, epoxy resin, polycarbonate, acryl-based resin, methacrylic resin, polyurethane, and poly(vinyl chloride). In general, a plate-shaped substrate having no flexibility is used as the insulating substrate, but an insulating substrate having flexibility may also be used. Moreover, the substrate itself may constitute an insulating material or it may constitute an insulating layer, such as an oxide layer, over a different insulating or conducting material. Preferably, the insulating substrate is an n-type semiconductor substrate, such as a silicon substrate having a thermal oxide film ($SiO_2$) or a p-type semiconductor substrate, such as a highly-doped p-type Si substrate ($p^+$-Si substrate), with a thermal oxide film on its surface.

The thickness of the insulating substrate (layer) is not limited to a specific thickness as long as it is strong enough to bear depositing the metal layer, but preferably ranges from 10 nm to 1 micrometer, more preferably from 100 nm to 500 nm, still more preferably from 200 nm to 400 nm, and particularly preferably 300 nm. Here, in this specification, the "thickness" means an average thickness of a predetermined portion to be measured. The insulating substrate may be manufactured by any suitable manufacturing method according to its material or a commercially available insulating substrate may be used.

Any suitable material may be used for the electrode 2 layer. A material constituting an electrode is not limited to a special material as long as it is conductive. For example, a metal film deposited on the insulating substrate by evaporation or other suitable methods, such as CVD, sputtering or MBE may be used. A metal used for the electrode is not limited to a special metal as long as it has a property of passing current. Preferably, metals that are selectively etched by the below described dry etching process but are not significantly etched by the below described wet etching process can be used for the metal constituting the electrode. Among such metals are noble metals having an excellent acid resistance, such as gold and platinum, a mixture of these metals, an alloy of these metal and other noble metals. Gold or platinum are the preferred electrode metals.

The electrode layer 2 may have any suitable thickness. If the electrode layer is too thick, it takes too much time to dry etch the electrode layer and it is difficult to make a microscopic nano-gap electrode. If the electrode layer is too thin, then the FIB may change the characteristics of the substrate below the electrode. Thus, it is preferable that the thickness of the electrode layer is larger than an ion penetration depth of the FIB so as to prevent the characteristics of the insulating substrate in the gap from being changed by ion implantation. Preferably, the electrode layer thickness ranges from 1 nm to 500 nm. Further, more preferably, the thickness of the electrode layer ranges from 10 nm to 400 nm, still more preferably from 50 nm to 100 nm, and particularly preferably, 70 nm.

As for a method of forming the electrode layer, any suitable metal thin film forming method can be used, depending on the kind of metal used for the electrode layer.

Such metal thin film forming methods include a vacuum vapor-deposition method of heating and evaporating a metal in a vacuum and thereby depositing the metal on a substrate, a sputtering method of applying an inert gas plasma to a target and thereby depositing sputtered atoms on a substrate, a physical vapor deposition method such as an ion plating method of performing vapor-deposition in an ionized atmosphere, and a chemical vapor deposition method such as a chemical vapor deposition method in which halogenide is made to react with a heated substrate to deposit metals onto the substrate, a plasma CVD method, and a MOCVD method. Among these methods, it is preferable that a metal thin film is deposited on the insulating substrate by the sputtering method. If the metal electrode layer is made of an anodizable metal, then insulating regions in the electrode layer may be selectively formed by anodic oxidation method of forming an oxide film on an anode by electrolysis.

Any suitable material may be used for the metal mask layer 3, which has a physical property different from the above-mentioned electrode layer 2. For example, a metal which can be selectively etched by wet etching compared to the metal of the electrode layer and which is significantly more resistant to dry etching than the electrode layer metal is preferably used. Furthermore, a metal having higher ionization tendency than the metal used for the electrode layer or a metal harder than the metal used for the electrode layer can be used. If the metal mask layer is formed of such a metal, in the wet etching step, the metal mask layer is completely removed under conditions where the electrode layer is not removed.

Thus, it is preferable that a metal resistant to dry etching be used for the metal mask layer, and to be more specific, that a metal harder than the metal used for the electrode layer be used. A ratio of hardness between the metal used for the metal mask layer and the metal constituting the electrode layer preferably ranges from 9/8 to 10/1, more preferably, from 2/1 to 6/1 and particularly preferably, from 3/1 to 5/1.

Among such metals are, for example, metals such as Sc, Y, Ti, Zr, Hf, V, Nb, Ta, Cr, Mo, W, Mn, Tc, Re, Fe, Ru, Os, Co, Rh, Ir, Ni, Pd, Zn, Al, Ga, In, Tl, Sn, Pb, Li, Na, K, Rb, Cs, Fr, Be, Mg, Ca, Sr, Ba, and Ra, and mixtures and alloys of these metals. Among these metals, Ti, W, Al, and Zr are preferable and Ti is particularly preferable.

The thickness of the metal mask layer depends on its kind but is not limited to a specific thickness as long as the metal mask layer is durable when it is subjected to dry etching. Then, the thickness of the metal mask layer preferably ranges from 10 nm to 400 nm, more preferably from 20 nm to 200 nm, still more preferably from 30 nm to 60 nm, and particularly preferably 45 nm. This enables using an ion beam at low acceleration voltage and hence using a comparatively thin metal electrode. Moreover, using the metal mask reduces the width of the gap when the electrode is etched and hence enables manufacturing a microscopic nano-gap electrode. The metal mask layer may be manufactured by the same method as used in manufacturing the above-mentioned electrode layer.

Figure 3:
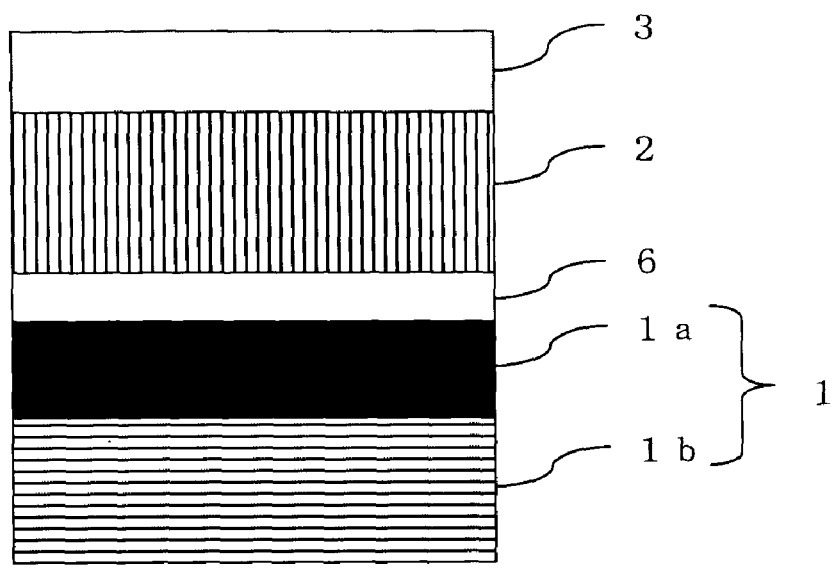
FIG. 3 shows the structure of a sample used in an example 1.

If desired, an optional adhesion layer 6 may be interposed between the insulating substrate 1 and the electrode layer 2 and/or between the electrode layer 2 and the metal mask layer 3 so as to enhance the adhesion of the respective layers, as shown for example in FIG. 3. It is preferable that this kind of adhesion layer be provided particularly between the insulating substrate and the electrode layer. Then, Pt, Au, Cr, Ti, and a mixture or alloy of these metals can be used as the adhesion layer. For example, Pt or a mixture of Pt and Au is deposited in a thickness from 1 nm to 50 nm, more preferably from 5 nm to 30 nm, still more preferably from 10 mm to 20 nm.

Respective patterning steps in the first embodiment are now described. In the mask layer patterning step, the metal mask layer is etched by using the focused ion beam (FIB) thereby to form a nano-gap electrode mask pattern.

Any suitable ion beam can be used as an ion beam constituting the focused ion beam. For example, any suitable cation can be used as an ion species constituting the focused ion beam. Preferably, the cation includes a $Ga^+$ ion and the like. In a conventional method of applying an electron beam to an organic resist layer (mask layer), the electrons applying to the organic resist layer are scattered and the organic resist layer is over exposed by the scattered electrons. As a result, the organic resist layer is exposed by the electrons in an expanded region near the periphery of the region which is intended to be exposed by the electron beam, thereby making it difficult to form a fine mask pattern. However, according to the preferred embodiments of the invention, the ion beam is exposed to the metal mask layer, so it is possible to prevent such scattering. Thus, it is possible to form a fine mask pattern and hence to form a nano-gap electrode having a narrow gap or another nanostructured layer having features that are 10 nm or less in size, such as openings or vias that are 10 nm wide or less.

It is preferable that the minimum diameter of the focused ion beam is small. The minimum diameter of the focused ion beam preferably ranges from 5 nm to 100 nm, more preferably from 5 nm to 30 nm, still more preferably from 5 nm to 15 nm, still more preferably from 5 nm to 10 nm, and particularly preferably is not larger than 10 nm.

The focused ion beam preferably has an ion speed of a certain level. An acceleration voltage applied to the ions so as to develop the ion speed which depends on the weight of the ion to be accelerated and preferably ranges from 10 kV to 2000 kV, more preferably from 20 kV to 80 kV, and still more preferably from 25 kV to 40 kV. In the first embodiment, the metal mask layer thicker than the penetration length of the ion is preferably used, so that it is possible to use an ion beam at a low acceleration voltage and hence to manufacture a thin electrode layer without impairing the insulating ability of the insulating substrate.

In the FIB etching step, it is preferable that the ions applied to the metal mask layer are provided in a desired quantity. Thus, the total number of radiated ions per an area 1 cm square of the metal mask layer depends on the hardness and thickness of the metal mask layer and preferably ranges from $10^{12}$ to $10^{14}$, more preferably from $10^{16}$ to $10^{20}$, still more preferably from $5\times10^{16}$ to $10^{19}$, and particularly preferably from $10^{17}$ to $10^{18}$. In a conventional lithography using an organic resist, the number of ions of $10^{15}$ to $10^{21}$ is sufficient, but in the preferred embodiments of the invention, it is preferable that a larger number of ions be applied to the metal mask layer so as to etch the metal layer.

Among specific apparatuses for forming a focused ion beam, JFIB-2300 made by Seiko Instruments Inc., may be used.

In consideration of undulations existing on the boundary surface between the metal mask layer and the electrode layer, in order to completely remove portions to be removed by the etching of the metal mask layer, etching the surface of the electrode layer to a certain extent is another preferable embodiment of the invention. The depth to be etched in this manner of the electrode layer preferably ranges from 1 nm to 40 nm, more preferably from 10 nm to 30 nm, still more preferably from 15 nm to 25 nm, and particularly preferably 20 nm.

The step of transferring a pattern to the electrode layer by using the mask manufactured in the above-mentioned FIB step will now be described. An etching gas for selectively etching the electrode layer is used. Such etching methods include, for example, a method of making a gas or an ion gas impact against the metal mask layer and a method of making the reactive gas react on the metal mask layer. Preferably, this step comprises dry etching by sputter etching using $Ar^+$ ions. In order to make a microscopic gap electrode, preferably, an electric field is vertically applied to the substrate to accelerate ions thereby to anisotropically etch the exposed portion(s) of the electrode layer. This kind of etching can be performed, for example, by an ion shower apparatus (Ellionics EIS-200ER). For example, in a case where Ti is used for the metal mask layer and Au is used for the electrode layer, Ti has a lower etching rate than Au and hence Ti is hardly etched. Thus, the Au electrode can be patterned by adjusting an etching time or other conditions.

The step of selectively removing the metal mask layer by wet etching, such as by an acid or the like will now be described. Here, an etching solution is used which easily dissolves the metal mask layer and hardly dissolves the electrode layer, the adhesion layer, if present, and the insulating substrate. This kind of etching solution is not limited to a particular acid and includes an acid solution containing sulfuric acid such as a mixed solution of sulfuric acid and hydrogen peroxide. In the wet etching step, the electrode produced in the above-mentioned electrode is dipped in the acid. For example, the Au electrode (or a Au/Pt electrode) and a $SiO_2$ film which acts as a substrate are not significantly etched by the above-mentioned acid. Thus, by using the above-mentioned acid, only the Ti mask layer can be removed. In this manner, the nano-gap electrode can be manufactured.

The following specific example is provided for illustration only and should not be deemed to be limiting on the scope of the invention. FIG. 3 shows the structure of a sample of specific example 1. A highly doped p-type Si (p$^+$-Si) substrate 1b having a thermal oxide (SiO$_2$) film 1a of about 300 nm thick is used as an insulating substrate. A Pt layer 6 (12 nm) used as an adhesion layer is located between an Au electrode layer 2 and the insulating substrate 1b. The Au layer (70 nm) is used as an electrode layer 2, and a Ti layer (45 nm) is used as a metal mask layer 3. Layers 2 and 3 are vacuum evaporated in this order onto the thermal oxide (SiO$_2$) film 1a by a sputter vapor-deposition method to manufacture a Ti/Au/Pt/SiO$_2$/p$^+$-Si structure.

Figure 1:
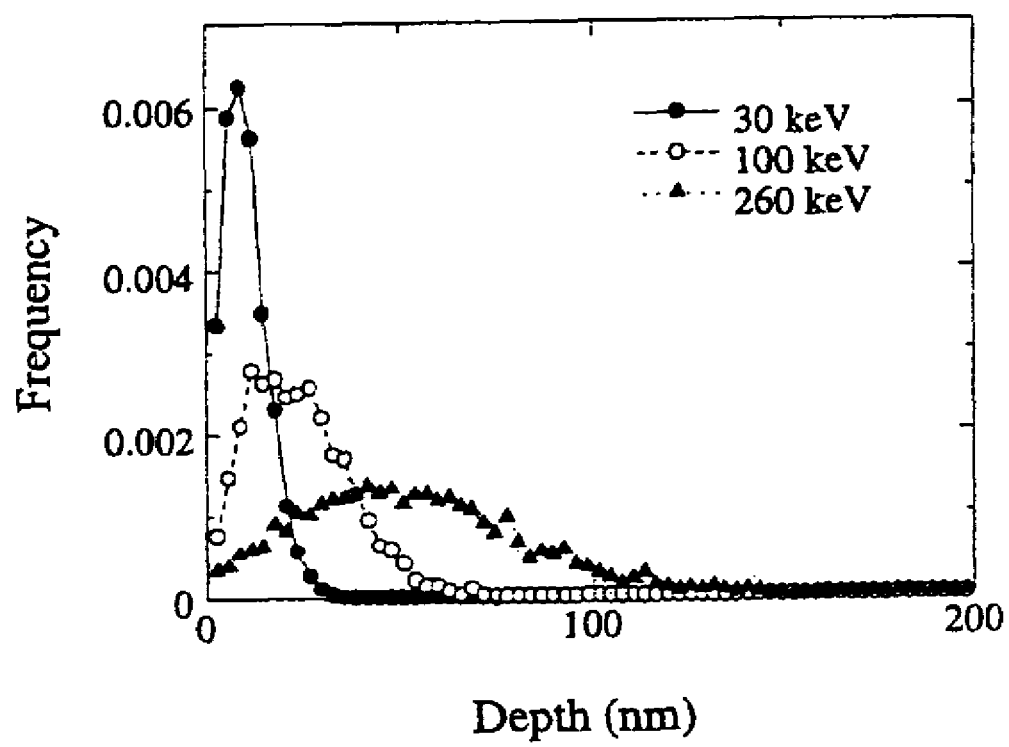
FIG. 1 shows the numerical simulation result of a Ga$^+$ ion penetration depth into a Au substrate by using a TRIM program.

A FIB-2300 FIB apparatus made by Seiko Instruments Inc. having a Ga$^+$ ion source having an acceleration voltage of 30 kV is used as the FIB source. The minimum diameter of a focused ion beam is about 12 nm. The upper Ti layer is exposed with ions at a dose of $10^{17}$ to $10^{18}$ ions/cm$^2$ by the using this FIB apparatus to etch the Ti layer thereby to form a mask pattern. The major portion of the electrode layer is etched by a large-diameter beam and only a nano-gap is etched by a minimum-diameter beam because it takes several hours to etch the whole electrode by using the minimum-diameter beam. In the actual etching, because undulations are formed on the interface of the Ti mask layer and the Au electrode layer, in order to remove the Ti mask completely, it is also preferred that the Au electrode layer be etched by about 20 nm. It is possible that ions passing through the Au electrode layer might reach the SiO$_2$ insulating layer. However, since the ion penetration depth into the metal of large mass such as Au and Pt is about 30 nm in a case of using Ga$^+$ ions at an acceleration voltage of 30 kV (see FIG. 1), it is considered that the ion implantation into the SiO$_2$ insulating film is negligible.

Dry etching the Au/Pt electrode layer by using the Ti mask is performed by sputter etching using Ar$^+$ ions. In order to manufacture a more microscopic gap electrode, an ion shower apparatus (Ellionics EIS-200ER) is used which accelerates ions by an electric field vertical to the substrate and thereby anisotropically etches the electrode layer. Ti has a lower etching rate than Au and Pt and hence Ti is hardly etched. The Au/Pt electrode layer is patterned by adjusting an etching time and other conditions.

The Ti mask metal after patterning the electrode is dipped in a mixed solution of sulfuric acid and hydrogen peroxide for several tens of minutes, thereby being removed. Here, the Au/Pt electrode layer and the SiO$_2$ insulating film are not active in etching because of etching selectivity and hence Ti can be selectively removed.

In order to perform the electric measurement of the nano-gap electrode, the nano-gap manufactured by the FIB is connected to a pad electrode. The pad electrode is manufactured by photolithography. The Au/Pt/SiO$_2$/p$^+$-Si structure having the nano-gap formed in the Au and Pt layers is coated with a photoresist by a spin coating method and then the nano-gap is aligned with a pad electrode mask by using a mask aligner and then exposed by light. After development, the Au/Pt electrode is etched and patterned by sputter etching using Ar$^+$ ions to manufacture the nano-gap electrode.

After the photoresist is separated, the manufactured nano-gap electrode is cleaned by O$_2$ plasma so as to remove the organic resist substances completely. Then the structure is dipped in a mixed solution of sulfuric acid and hydrogen peroxide or concentrated sulfuric acid for several hours, then is cleaned by acetone, methanol and de-ionized water and finally is cleaned by UV ozone for several hours.

The current-voltage characteristics of the nano-gap electrode are measured with a standard two terminal technique using a DC source (Advantest TR6143) and an electrometer (KEITHLEY 6517A).

After the measurement of electric characteristics, the nano-gap electrode is observed using a field emission scanning electron microscope (SEM) (JEOL JSM-6700F)

FIG. 4A shows the SEM image of the Au/Pt nano-gap electrode manufactured on the SiO$_2$ substrate. FIG. 4B shows an enlarged view of the nano-gap electrode in FIG. 4A. It is evident from FIG. 4B that the nano-gap electrode having a gap of about 5 nm could be manufactured. It is found that, a gap smaller than the minimum beam diameter of the FIB (about 12 nm) can be manufactured. It is considered that ion-etching with the top of FIB forms such narrow gaps.

Figure 4:
FIG. 4A is a scanning electron microscope (SEM) image of a Au/Pt nano-gap electrode fabricated on a SiO$_2$ substrate.
FIG. 4B is an enlarged diagram of opposed electrode portions of the nano-gap electrode in FIG. 4A.
Figure 4:
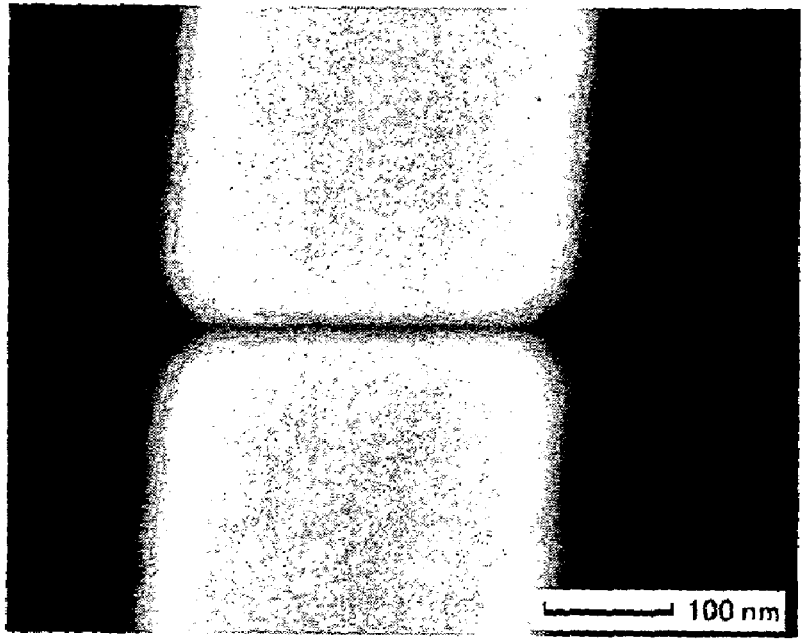
Figure 5:
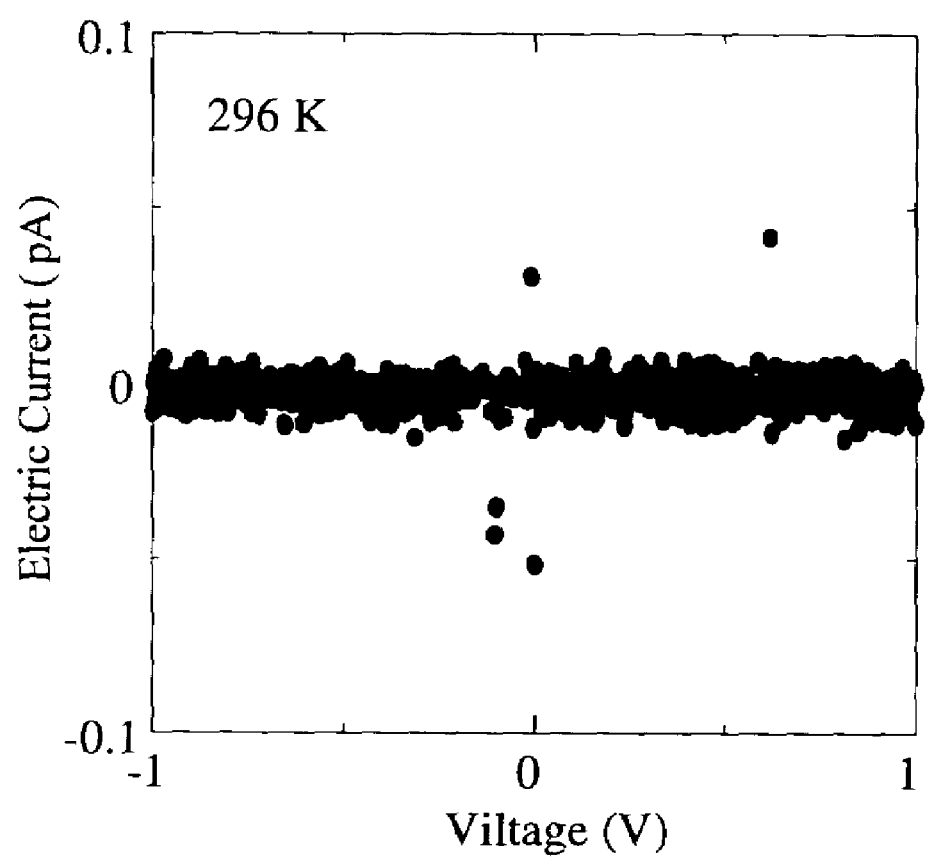
FIG. 5 shows the current-voltage characteristics of the nano-gap electrode produced in the example 1.

FIG. 5 shows the current-voltage characteristics of the nano-gap electrode in FIG. 4. The measurement is performed at room temperature (296 K) in vacuum. In order to prevent the electric characteristics from being changed by the SEM observation, the measurement is performed before the SEM observation. The obtained current is of the order of pA and hence the nano-gap electrode is sufficiently insulated.

In the present embodiment, in order to manufacture a nano-gap electrode capable of measuring the electric conduction characteristics of a single organic molecule, the nano-gap electrode is manufactured by a new nano-gap electrode manufacturing method using the FIB. As a result, a Au/Pt nano-gap electrode having a gap length of about 5 nm could be manufactured on the SiO$_2$ insulating film. Then, as a result of measuring the electric conduction characteristics, it is found that the nano-gap electrode is sufficiently insulated. Here, since the FIB having a minimum diameter of 12 nm is used, it is possible to produce the nano-gap electrode whose opposed electrode portions have a gap of 5 nm. That is, according to the preferred embodiments of the invention, it is possible to produce the nano-gap electrode whose opposed electrode portions have a gap being equal to one half or less of the minimum diameter of the FIB. For example, at present, an apparatus is developed which can control the minimum diameter of a FIB to about 4 nm or 5 nm, so if such an apparatus is used, it is possible to produce a nano-gap electrode whose opposed electrode portions have a gap of 2 nm or 2.5 nm.

According to the preferred embodiments of the invention, since a metal layer is used instead of a conventional organic resist, it is possible to produce an electrode whose two electrode portions have a microscopic gap (nano-gap electrode) without impairing the insulating ability of an insulating substrate. The nano-gap electrode manufactured by a nano-gap electrode manufacturing method of the preferred embodiments of the invention can be used for measuring the electric conduction characteristics and the like of an organic molecule.

The preferred embodiments of the invention include a step of forming an adhesion layer for enhancing the adhesion of the insulating substrate and the electrode layer and this adhesion layer may act as the electrode layer. Since the adhesion layer can enhance the adhesion of the insulating substrate and the electrode layer, it is possible to prevent the electrode layer from being separated from the insulating substrate.

In the preferred embodiments of the invention, by making the thickness of the metal electrode layer larger than a maximum ion penetration depth, that is, a depth when the focused ion beam is most deeply penetrated into a electrode layer in a mask pattern forming step, it is possible to prevent the characteristics of the insulating substrate in the gap from being changed by ion implantation.

In the preferred embodiments of the invention, by removing not only the metal mask layer but also the electrode layer by a depth from 1 nm to 40 nm on the average in the above-mentioned mask pattern forming step, it is possible to effectively remove the metal mask layer including some undulations formed on the boundary surface between the metal mask layer and the electrode layer.

While the term "nano-gap electrode" is used in a singular tense, the two portions of the nano-gap electrode may be connected to different current or voltage terminals or to the same current or voltage terminal (i.e., they may be connect to each other in a location away from the nano-gap). If the two portions of the nano-gap electrode are connected to different current or voltage terminals and one or more organic molecules connected the portions of the electrode across the nano-gap, then a molecular memory or logic device may be formed. Furthermore, nanostructure layers with openings having a size of 2–12 nm other than nano-gap electrodes may be formed by the method of the preferred embodiments of the present invention.

The foregoing description of the invention has been presented for purposes of illustration and description. It is not intended to be exhaustive or to limit the invention to the precise form disclosed, and modifications and variations are possible in light of the above teachings or may be acquired from practice of the invention. The description was chosen in order to explain the principles of the invention and its practical application. It is intended that the scope of the invention be defined by the claims appended hereto, and their equivalents.

What is claimed is:

1. A method of manufacturing a nano-gap electrode comprising:
   depositing an electrode layer and a metal mask layer in this order on an insulating substrate;
   etching the metal mask layer using a focused ion beam and thereby forming a mask pattern;
   transferring the mask pattern to the electrode layer by dry etching the electrode layer to form the nano-gap electrode; and
   selectively removing the metal mask layer from the nano-gap electrode by selective wet etching,
   wherein the thickness of the electrode layer is larger than a maximum ion penetration length of the focused ion beam in the mask pattern forming step.

2. The method of claim 1, further comprising a step of forming an adhesion layer between the insulating substrate and the electrode layer for enhancing adhesion of the electrode layer to the insulating substrate.

3. The method of claim 1, wherein the thickness of the metal mask layer ranges from 10 nm to 400 nm.

4. The method of claim 1, wherein ions impact against the metal mask layer at a dose from $10^{15}$ to $10^{21}$ ions/cm$^2$ in the mask pattern forming step.

5. The method of claim 1, wherein not only the metal mask layer but also the electrode layer is removed by 1 nm to 40 nm on an average in the pattern forming step.

6. The method of claim 1, wherein a gap between electrode portions ranges from 2 nm to 12 nm.

7. The method of claim 1, wherein the metal mask layer comprises Ti.

8. The method of claim 1, wherein the electrode layer comprises Au.

9. The method of claim 1, wherein the focused ion beam comprises a gallium ion beam accelerated by an applied voltage from 10 kV to 200 kV.

10. The method of claim 1, wherein the focused ion beam has a minimum diameter from 5 nm to 100 nm.

11. The method of claim 1, wherein the gap between electrode portions is less than one half of the minimum focused ion beam diameter.

12. The method of claim 1, wherein the gap between electrode portions ranges from 2 nm to 10 nm.

13. The method of claim 1, wherein the gap between electrode portions ranges from 4 nm to 6 nm.

14. A method of manufacturing a nano-gap electrode whose two electrode portions have a gap ranging from 4 nm to 6 nm comprising:
   a deposition step of vacuum vapor-depositing a Pt layer from 10 nm to 15 nm in thickness as an adhesion layer, an Au layer from 60 nm to 80 nm in thickness as an electrode layer, and a Ti layer from 40 nm to 50 nm in thickness as a metal mask layer by a sputter vapor-deposition method in this order on an insulating substrate from 200 nm to 400 nm in thickness;
   a mask pattern forming step of making Ga$^+$ ions impact against the metal mask layer at a dose from $10^{17}$ to $10^{18}$ ions/cm$^2$ by using a focused ion beam including the Ga$^+$ ions and having a minimum diameter from 10 nm to 15 nm and accelerated by an acceleration voltage from 25 kV to 40 kV and thereby etching the metal mask layer and forming a mask pattern; and
   a dry etching step of etching an electrode layer including the Au layer and the Pt layer by sputter etching using Ar$^+$ ions and thereby patterning the electrode layer; and
   a wet etching step of dipping the metal mask layer in an acid water solution containing sulfuric acid and thereby removing the metal mask layer,
   wherein the thickness of the electrode layer is larger than a maximum ion penetration length of the focused ion beam in the mask pattern forming step.

15. The method of claim 14, wherein the thickness of the insulating substrate is 300 nm, the thickness of the Pt layer is 12 nm, the thickness of the Au layer is 70 nm, the thickness of the Ti layer is 45 nm, the acceleration voltage of the Ga$^+$ ions is 30 kV, the minimum diameter of the Ga$^+$ ion beam is 12 nm, and the gap between two electrode portions of the nano-gap electrode is 5 nm.

16. A method of making a nanostructured layer, comprising:
   providing a substrate comprising a first layer located over the substrate and a metal mask layer over the first layer;
   etching the metal mask layer using focused ion beam and thereby forming a mask pattern; and
   selectively etching an exposed portion of the first layer using the mask pattern as a mask to form an opening having a size of 2 nm to 12 nm in the first layer,
   wherein the thickness of the electrode layer is larger than a maximum ion penetration length of the focused ion beam in the mask pattern forming step.

17. The method of claim 16, further comprising selectively removing the metal mask layer from the etched first layer.

18. The method of claim 16, wherein:
   the first layer comprises a metal electrode layer;
   the step of selectively etching an exposed portion of the first layer comprises selectively dry etching the metal electrode layer;

the step of selectively removing the metal mask layer comprises selectively wet etching the metal mask layer; and the opening comprises a nano-gap in the metal electrode layer having a size of 2 nm to 10 nm.

19. The method of claim 16, further comprising placing an organic molecule in the opening in the first layer, wherein the first layer comprises a conductive layer.

* * * * *